United States Patent [19]  [11] 4,068,072
Tsushima et al.  [45] Jan. 10, 1978

[54] PROCESS FOR PRODUCTION OF 6-AMINOPENICILLANIC ACID OR 7-AMINOCEPHALOSPORANIC ACID DERIVATIVES

[75] Inventors: Susumu Tsushima; Norichika Matsumoto; Mitsuo Numata, all of Osaka, Japan

[73] Assignee: Takeda Chemical Industries, Ltd., Osaka, Japan

[21] Appl. No.: 701,731

[22] Filed: June 30, 1976

Related U.S. Application Data

[63] Continuation of Ser. No. 536,917, Dec. 27, 1974, abandoned.

[30] Foreign Application Priority Data

Dec. 27, 1973 Japan .................................... 48-1171

[51] Int. Cl.² .................. C07D 501/02; C07D 499/42

[52] U.S. Cl. ........................................ 544/19; 544/26; 260/306; 260/7 C; 260/239.1

[58] Field of Search .................... 260/243 C, 306.7 C

[56] References Cited

FOREIGN PATENT DOCUMENTS 788,750  9/1972  Belgium .......................... 260/243 C Primary Examiner—Nicholas S. Rizzo
Attorney, Agent, or Firm—Wenderoth, Lind & Ponack

[57] ABSTRACT

A derivative of 6-aminopenicillanic acid or 7-aminocephalosporanic acid is produced by a process which comprises chlorinating or brominating a 6-thioacylaminopenicillanic acid or 7-thioacylaminocephalosporanic acid compound to obtain a corresponding iminothiohalide compound, and then solvolyzing the iminothiohalide compound. The process is novel and industrially feasible for producing the amino compound, which is not accompanied by "reconversion reaction".

42 Claims, No Drawings

PROCESS FOR PRODUCTION OF 6-AMINOPENICILLANIC ACID OR 7-AMINOCEPHALOSPORANIC ACID DERIVATIVES

This application is a continuation of Ser. No. 536,917, filed Dec. 27, 1974, now abandoned.

The present invention relates to a process for production of amino compounds, more particularly to a novel and industrially feasible process for production of derivatives of 6-aminopenicillanic acid or 7-aminocephalosporanic acid of the following general formula (I), which are useful as intermediates for the synthesis of a variety of synthetic penicillins and cephalosporins;

$$H_2N-A \qquad (I)$$

wherein A is the residue of a 3-cephem or penam compound.

The process of the present invention, by which the above object amino compound (I) can be produced, comprises chlorinating or brominating a compound of the general formula III

wherein $R^1$ is an organic residue and A has the same meaning as above, to obtain a compound of the general formula (II)

wherein X is a chlorine or bromine atom and $R^1$ and A have the same meaning as above, and then, solvolyzing the compound (II).

The reactions involved in the present process are shown in the following schema:

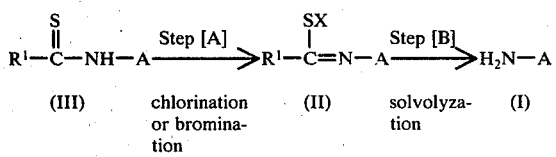

wherein A, $R^1$ and X have the same meaning as above.

Heretofore, 6-aminopenicillanic acid and 7-aminocephalosporanic acid compounds (I) have been produced, for example, by the method comprising halogenating penicillin G or cephalosporin C to obtain the corresponding imino-halide, then reacting the imino-halide further with an alcohol to obtain an iminoether compound and finally solvolyzing the imino-ether compound (Japanese Patent Publications No. 13862/1966, No. 27391/1969, No. 40899/1970, etc.). However, known also is the fact that a "reconversion" reaction, which reproduces the starting acylamido compound from the imino-ether compound, takes places as a side reaction in the course of said solvolysis (Japanese Patent Application Laid Open No. 62792/1974, German Patent Application No. P 2258079.6). Further, in these methods the imino-etherification reaction must be carried out at an extremely low temperature, or specific alcohols must be employed as solvents for said solvolysis, in order to obtain the object compound in good yield.

Previously, as a means for cleavage of the acyl group of 7-acylaminocephalosporanic acid derivatives, which is not accompanied with such reconversion reaction as above, some of the present inventors developed a process involving the route via the thioacylamido-compound (Japanese Patent Application Laid Open No. 34898/1973; Japanese Patent Application No. 56235/1972 and No. 66527/1972, German Patent Application No. P 2244620.4). However, this process is also accompanied with such drawback as troublesome handling of intermediates, because in this process the intermediate thioacylamido compound must be isolated or separated prior to the next reaction step, and in this process so-called one-batch procedure starting from the corresponding acylamido compound can not be applied. Thus, these known methods for the production of the amino compound (I) are not satisfactory from an industrial point of view such as yield, handling of intermediates, reaction temperature and kind of solvents used for said solvolysis.

Under these circumstances, the present inventors have made extensive studies for developing a novel and advantageous route for the production of the amino compound (I).

As the result of the studies, the present inventors have quite unexpectedly found out that a thioacylamido compound (III) is chlorinated or brominated to give a corresponding novel iminothiohalide (II), and the iminothiohalide (II) is easily solvolized, even by readily available alcohol from an industrial point of view, such as methanol, to give an amino compound (I) at not so low a temperature, in good yield and without any substantial reconversion reaction. Further it has also been found that the compound (III) is employable as a starting compound of the reaction of Step (A) without prior isolation or purification thereof. As the result of these factors, the object aminocompound (I) is produced in a good yield in this process.

The present invention has been accomplished on the basis of these findings. Thus, according to the present process, the object amino compound (I) can be easily produced in a good yield by simple procedure and therefore the present process is remarkably feasible, effective and advantageous from an industrial point of view.

Namely, the principal and essential object of the present invention is to provide a novel and industrially feasible process for producing the amino compound (I), and this object can be attained by the process described in detail hereinafter.

In the above general formula, the organic residue represented by $R^1$ is a group capable of forming a thioacyl group with an adjacent thiocarbonyl group, which is derived from an acylamido group in 6-position of a penicillin derivative or 7-position of cephalosporin derivative by eliminating the — CONH — group. Among such organic residues are included those whose functional group, such as amino or/and carboxy, have been suitably protected. As the typical examples of those organic residues, there may be phenyl, thienylmethyl, benzyl, phenoxymethyl or 4-amino-4-carboxybutyl group whose amino or/and carboxy group may be protected. Among above, benzyl or 4-amino-4-carboxybutyl group whose amino or/and carboxy group may be protected is preferable as the organic residue $R_1$.

As the protective group for amino group, there may be mentioned, among others, lower acyl (e.g. acetyl, propionyl), benzoyl, phenylacetyl, phenoxyacetyl, benzyloxycarbonyl, phthaloyl, isobornyloxycarbonyl, pivaloyl, p-(t-butyl)benzoyl, p-toluenesulfonyl, p-(t-butyl)benzenesulfonyl, camphorsulfonyl, etc.

Among the above, phthaloyl, isobornyloxycarbonyl, p-(t-butyl)-benzoyl or p-(t-butyl)benzenesulfonyl is preferable as the protective group for free amino group.

The residue of penam compound which is represented by A is a penicillin moiety derived by eliminating the 6-acylamino group thereof, which is represented by the formula:

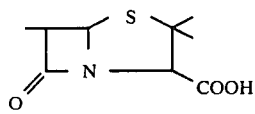
(V)

or a group corresponding to (V) whose carboxyl function has been previously protected. As the residue of 3-cephem compound, use is made of a cephalosporin moiety derived by eliminating the 7-acylamino group thereof, which is represented by the general formula:

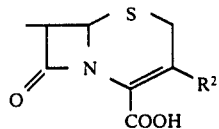
(VI)

wherein $R^2$ is a group which does not take part in the present reaction, or a group corresponding to (VI) whose carboxyl function has been previously protected. The group which does not take part in the present reaction is a group which is not affected by the reaction of this invention. As typical examples of the group represented by $R^2$, there may be mentioned, among others, lower alkyl (e.g. methyl, ethyl, propyl); lower alkoxymethyl(e.g. methoxymethyl, ethoxymethyl, propoxymethyl); lower acyloxy methyl (e.g. acetoxymethyl, propionyloxymethyl); a group represented by —$CH_2SR^3$ in which $R^3$ stands for lower alkyl (e.g. methyl, ethyl or propyl) or a nitrogen-containing heterocyclic group containing not less than one nitrogen atom which may be in the oxide form or, in addition to a nitrogen atom or nitrogen atoms, such other atoms as oxygen or/and sulfur atoms. The nitrogen-containing heterocyclic group desirably has 1 to 4 hetero atoms selected from the group consisting of nitrogen, oxygen and sulfur atoms in its heterocyclic ring, and the ring may be 5 or 6 membered.

As such nitrogen-containing heterocyclic group, there may be mentioned, among others, pyridyl, N-oxido-pyridyl, pyrimidyl, pyridazinyl, N-oxido-pyridazinyl, pyrazolyl, thiazolyl, thiadiazolyl such as 1,2,3-thiadiazolyl, 1,2,4-thiadiazolyl, 1,3,4-thiadiazolyl or 1,2,5-thiadiazolyl, oxadiazolyl such as 1,2,3-oxadiazolyl, 1,2,4-oxadiazolyl, 1,3,4-oxadiazolyl or 1,2,5-oxadiazolyl, triazolyl such as 1,2,3-triazolyl or 1,2,4-triazolyl, tetrazolyl such as 1H-tetrazolyl or 2H-tetrazolyl and others. Each of these nitrogen-containing heterocyclic groups may be further substituted in its optional position by a substituent such as, for example, a monovalent group, for example, lower alkyls having 1 to 4 carbon atoms such as methyl, ethyl, trifluoromethyl, propyl, isopropyl, butyl, isobutyl, etc.; lower alkoxyls having 1 to 4 carbon atoms such as methoxy, ethoxy, propoxy, isopropoxy, butoxy, etc.; halogens such as chlorine, bromine, etc.; amino; mercapto; hydroxyl; carbamoyl; or carboxy group. As additional examples of the substituents of the heterocyclic group, there may also be mentioned, among others, monovalent group, for example, a substituted lower alkyl group such as substituted methyl, ethyl or propyl, a substituted mercapto. group or a mono- or di-substituted amino group. The substituents of such a substituted lower alkyl group may be hydroxyl, mercapto, amino, morpholino, carboxy, sulfo, carbamoyl, alkoxycarbonyl, mono- or di-lower alkylcarbamoyl, alkoxy, alkylthio, alkylsulfonyl, acyloxy or morpholinocarbonyl group, etc. In the substituents of the substituted lower alkyl group, the alkyl group is exemplified by methyl, ethyl or isopropyl; the alkoxy group is exemplified by methoxy, ethoxy, propoxy, butoxy, isobutoxy, hexyloxy, octyloxy, decyloxy or dodecyloxy; the acyloxy is exemplified by acetoxy, propionyloxy, valeryloxy, caproyloxy, benzoyloxy, phenylacetoxy. The substituents of the substituted mercapto group may be the same lower alkyl group or the same substituted lower alkyl group as mentioned above. The substituents of the mono- or di-substituted amino group may be carboxy, carbamoyl, or the same lower alkyl, alkoxycarbonyl, lower alkylcarbamoyl or substituted lower alkyl group as mentioned above.

As the substituents of the heterocyclic group mentioned above, specifically, use may be made of, for example, a substituted lower alkyl group such as carboxymethyl, an N-lower alkylcarbamoylmethyl (e.g. N,N-dimethylcarbamoylmethyl), a hydroxy-lower alkyl (e.g. hydroxymethyl, 2-hydroxyethyl), acyloxy-lower alkyl (e.g. acetoxymethyl, 2-acetoxyethyl,), an alkoxycarbonylmethyl (e.g. methoxycarbonylmethyl, hexyloxycarbonylmethyl, octyloxycarbonylmethyl), methylthiomethyl, methylsulfonylmethyl, an N-lower alkylamino-lower alkyl (e.g. N,N-dimethylaminomethyl, N,N-dimethylaminoethyl), morpholinomethyl, etc., mono- or di-substituted amino groups such as a lower alkylamino (e.g. methylamino), a sulfo-lower alkylamino (e.g. 2-sulfo-ethylamino), a hydroxy-lower alkylamino (e.g. hydroxyethylamino), a lower alkylamino-lower alkylamino (e.g. 2-dimethylamino-ethylamino), a lower alkoxycarbonylamino (e.g. methoxycarbonylamino), etc., a substituted mercapto group such as methylthio, 2-hydroxyethylthio, 2-acyloxytehythio(e.g. 2-acetoxyethylthio, 2-phenyl-acetoxyethylthio, 2-caproyloxyethylthio), carboxymethylthio, an alkoxycarbonyl-methylthio (e.g. methoxycarbonyl-methylthio, hexyloxycarbonyl-methylthio), an N-lower alkylcarbamyl-methylthio e.g. N,N-dimethylcarbamoyl-methylthio), an N-lower alkylamino-lower alkylthio, (e.g. 2-N,N-dimethylamino-ethylthio), morpholinocarbonylmethylthio, 2-sulfoethylthio, etc.

The group represented by $R^2$ also stands for an iminomethyl groups of the general formula (VII)

—CH=NOR⁴     (VII)

wherein $R^4$ is an unsubstituted or substituted alkyl group. As examples of the unsubstituted or substituted alkyl represented by $R^4$, there may be mentioned, among others, straight-chain, branched or cyclic alkyl groups having 1 to 6 carbon atoms (e.g. methyl, ethyl, propyl, isopropyl, n-butyl, i-butyl, sec-butyl, t-butyl, pentyl, heptyl, hexyl, cyclopentyl, cyclohexyl, etc.) and the said alkyl groups having 1 to 6 carbon atoms substituted by alkenyl, aryl (e.g. phenyl), 5 to 6 membered heterocyclic group having 1 to 2 hetero atoms selected from the group of consisting nitrogen, oxygen and sulfur atoms, carboxy or primary to quaternary amino groups (e.g. benzyl, furfuryl, 2-thienyl methyl, 3-thienyl methyl, allyl, tetrahydrofurfuryl, 2-pyridylmethyl, 3-pyridylmethyl, 4-pyridylmethyl, 2-pyridylethyl, 3-pyridylethyl, 4-pyridylethyl, carboxymethyl (—$CH_2$—COOH), $\beta$-dimethylaminoethyl, $\beta$-pyrrolidinoethyl, $\beta$-piperidinoethyl, $\beta$-cyanoethyl, pyridinium methyl, $\beta$-morpholinoethyl, $\gamma$-morpholinopropyl, etc.). Among the groups represented by the formula —$CH_2SR^3$, a group wherein $R^3$ is an unsubstituted or substiututed nitrogen-containing heterocyclic group is preferable. Further among the unsubstituted or substituted nitrogen-containing heterocyclic group, tetrazolyl, oxadiazolyl and thiadiazolyl groups are more preferable. As the protective group for the carboxy group of said organic residue $R^1$ or for the carboxy group of the residue of a 3-cephem or penam compound which is represented by A, there may be employed, among others, lower straight or branched alkyl having 1 to 6 carbon atoms (e.g. methyl, ethyl, tert-butyl, tert-amyl), aralkyl unsubstituted or substituted by nitro or lower alkoxy (e.g. benzyl, p-nitrobenzyl, p-methoxybenzyl), lower acyl (e.g. acetyl, propionyl), benzhydryl, 1-indanyl, phenacyl, phenyl, p-nitrophenyl, lower alkoxy alkyl (e.g. methoxymethyl, ethoxymethyl), acyloxy lower alkyl (e.g. benzyloxymethyl, acetoxymethyl), pivaloyloxymethyl, $\beta$-methylsulfonylethyl, methylthiomethyl, trityl, $\beta$, $\beta$, $\beta$-trichloroethyl, silyl groups (e.g. di or tri-lower alkylsilyl group such as trimethylsilyl, dimethylsilyl), phosphorus trichloride, etc. Further, said carboxy groups may each be employed in the form of an inorganic or organic salt with, for example, an alkali metal, or alkaline earth metal e.g. sodium, potassium or magnesium or the like, or any of various organic amines. As the said protective group for carboxy group, $\beta$-methylsulfonylethyl, phosphorus trichloride and silyl groups are preferable.

The reaction of Step [A] is carried out by chlorinating or brominating a compound (III) to compound (II). This chlorination or bromination is effected by reacting compound (III) with a chlorinating or brominating agent such as, for example, chlorine, bromine, sulfuryl chloride, sulfuryl bromide, N-chlorosuccinimide, N-bromosuccinimide, N-chlorophthalimide, N-bromophthalimide, t-butyl hypochlorite, trichloroisocyanuric acid, thionyl chloride, thionyl bromide, or the like. It is, of course, possible to employ such reaction conditions as will yield the a chlorinating or brominating agent in the course of the reaction.

The amount of the chlorinating or brominating agent to be used is not less than one mole equivalent relative to thioacylamido compound (III). Generally, use of the chlorinating or brominating agent an an amount of 1.5 moles relative to thioacylamido compound (III) is sufficient for the reaction of Step [A].

When the reaction of Step [A] is conducted immediately following the production of thioacylamido compound (III) without prior isolation or separation thereof, the said chlorinating or brominating agent is preferably used in a proportion of not less than one mole equivalent relative to the sulfur compound used in the production of thioacylamido compound (III), which is mentioned hereinafter.

The reaction of Step [A] is generally conducted in an organic solvent. As the solvent may be employed any of the solvents which will not react extensively with the chlorinating or brominating agent. Typical examples of said solvent include halogenated hydrocarbon (e.g. dichloromethane, chloroform, 1,2-dichloroethane), aromatic hydrocarbon (e.g. benzene, xylene, toluene), dioxane, ethylacetate, carbon disulfide, and acetonitrile.

The reaction is generally conducted at a temperature ranging from about $-30°$ to room temperature.

The reaction of Step [A] is carried out by subjecting the resultant novel intermediate compound (II) to solvolysis reaction. The solvolysis reaction comprises reacting compound (II) with solvolysis solvent. In the reaction, the intermediate compound (II) obtaned in Step [A] is preferably directly subjected to the solvolysis reaction without prior isolation. However, if desired, the compound (II) may be isolated or separated by conventional means (e.g. evaporation of the solvent used or column chromatography on silica gel), preferably at low temperature. As the solvent to be used for said solvolysis, there may be mentioned alcohols including lower aliphatic alcohols having 1 to 4 carbon atoms such as methanol, ethanol, propanol, butanol, i-butanol, glycols such as ethylene glycol, propylene glycol, 1,3-butanediol, triols such as glycerin, etc.; organic carboxylic acids such as acetic acid, propionic acid, etc.; mercaptans such as methylmercaptan, ethyl mercaptan, etc.; and water to name but a few. Particularly preferred of these solvents are the alcohols, and among the alcohols straight chained monohydric ones having 1 to 3 carbon atoms such as methanol or ethanol, especially methanol is most preferable. The amount of the solvent that is theoretically required for the solvolysis is 2 mole equivalents relative to compound (II), but better results are in many cases obtained when an excess of the solvent is employed.

This solvolysis is preferably conducted in the presence of an acid. As the acid, there may be employed inorganic acids such as mineral acid (e.g. hydrochloric acid, sulfuric acid; phosphoric acid, etc.) and organic sulfonic acids such as camphorsulfonic acid, toluenesulfonic acid, benzenesulfonic acid, etc. The amount of the acid to be used is generally not less than one mole equivalent relative to compound (II). Such an acid need not be added to the reaction system of Step [B] in cases where an acid is formed with the progress of the solvolysis reaction. While the solvolysis may be effected by producing the intermediate compound (II) beforehand and then adding a solvolysis solvent and an acid thereto, it may alternatively be carried out in such a manner that a solvolysis solvent and an acid are added prior to the production of the intermediate compound (II), i.e. the reaction of Step [A], so that the addition of a chlorinating or brominating agent will give rise to intermediate compound (II) which will then be substantially simultaneously solvolyzed.

This solvolysis reaction may be generally conducted at about $-30°$ C to room temperature but, being an exothermic reaction, the reaction is desirably carried out under cooling.

The amino-compound (I) thus obtained may be isolated in the conventional manner. Thus, when the product has separated out as an acid addition salt corresponding to the acid used or produced from the reaction system, it may be easily isolated by mere filtration. When the carboxy group thereof has been protected with a silylating agent or phosphorus trichloride, the object amino compound (I) may be easily isolated by decomposing the protected portion of the group of the reaction product with water and adjusting the pH of the resultant mixture to its isoelectric point.

The process of this invention involving the route via the novel intermediate compound (II) is a commercially very profitable process in that, unlike the process via iminoehter compound, it virturally does not entail a reconversion reaction and the reactions proceed in a single reaction vessel to give an amino-compound (I) in good yield even at mild temperatures.

The object amino compounds (I) thus produced are useful as intermediates for the synthesis of a variety of synthetic penicillins and cephalosporins. For example, by acylating the compounds (I), the cephalosporin derivatives having antibacterial properties and being useful as antibiotics are obtained as follows;

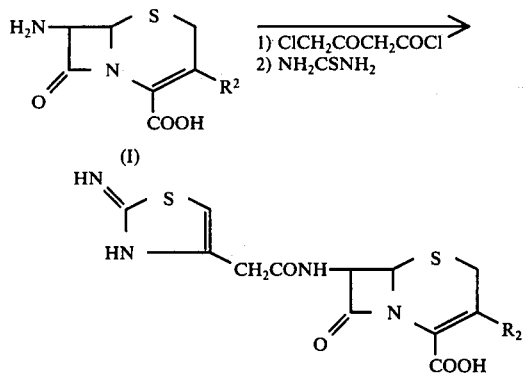

wherein $R_2$ has the same meaning as above.

The compound (III) of this invention may be produced, for example, by the procedure set forth in Japanese Patent Application Laid Open No. 34898/1973, from the corresponding acylamido compound (IV) as follows;

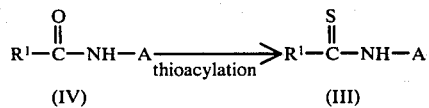

wherein $R^1$ and A have the same meaning as above.

The compound (IV) of this reaction can be easily produced by a fermentation process or can be easily derived from products of a fermentation process.

A compound (IV) wherein $R^2$ of the A. group is $-CH_2 SR^3$ may be produced by reacting a compound (IV) wherein $R^2$ is $-CH_2OCOCH_3$ with a corresponding mercaptan ($R^3SH$).

The thioacylation mentioned above comprises reacting compound (IV) with a sulfurizing agent such as phosphorus pentasulfide or, alternatively, by reacting compound (IV) with a halogenating agent such as phosphorus pentachloride to obtain the corresponding iminohalide compound and then reacting the product with a sulfur compound such as hydrogen sulfide, thiocarboxylic acid, thioacetamide or a phosphorous compound of the formula:

wherein $R^5$ and $R^6$ respectively represent an alkoxy (e.g. methoxy, ethoxy, propoxy) or dialkylamino group (e.g. dimethylamino).

The reaction of the compound (IV) with the sulfurizing agent is carried out in a solvent such as dichloromethane, chloroform, benzene, xylene, dioxane, ethyl acetate or carbon disulfide. This reaction is preferably conducted in the presence of a base, for example, pyridine, quinoline or N,N-dimethylaniline, generally at room temperature or under cooling with ice. The halogenating agent which is employed in the formation of the iminohalide compound may, for example, be phosphorus oxychloride, phosphorus pentachloride, phosphorustrichloride or thionyl chloride. The reaction leading to an iminohalide is generally conducted advantageously in a solvent such as chloroform or dichloromethane. This reaction is preferably carried out in the concomitant presence of an organic base such as pyridine, quinoline, N,N-dimethylaniline, triethylamine or N-methylmorpholine. As the proportion of said base, it is sufficient to add 2 to 3 equivalents based on the halogenating agent. Relative to the compound (IV), generally 1 to 2 equivalents of a halogenating agent is employed. This reaction leading to the formation of an iminohalide is preferably conducted at a temperature of about $-40°$ C to about 30° C and it is advantageous to arrange the reaction so that it goes to completion generally in about 15 to 120 minutes.

Subsequently, to the thus-obtained reaction mixture containing the iminohalide compound, is added a sulfur compound such as, for example, hydrogen sulfide, thioacetic acid, thioacetamide, or a phosphorous compound (VIII) such as dimethyl dithiophosphate, diethyl dithiophosphate, etc. The reaction with the sulfur compound proceeds within the above-mentioned temperature range to give the compound (III) is good yield. In adding the sulfur compound to the iminohalide compound, it is desirable to add simultaneously an acid acceptor such as an organic base, as mentioned in the preceding reaction. When suitable amount of hydrogen chloride and pyridine co-exists in the reaction system, the compound (III) precipitates as an adduct consisting of the compound, hydrogen chloride and pyridine (1:1:1).

In this invention said compound (III) may be subjected to the contemplated reaction of this invention either as it is in the reaction mixture obtained during its production, or after it has been previously subjected to a suitable purification process. However, the compound thus obtained is preferably subjected directly to the reaction of Step [A] without prior isolation or purification. Or the compound (III) may be subjected to the contemplated reaction in the form of an adduct to an equimolar amount each of hydrogen chloride and pyridine.

For further explanation of the present invention, the following Examples and References are given, wherein "part(s)" is based on weight unless otherwise noted and the relationship between "part(s)" and "volume part(s)" corresponds to that between "gram(s)" and "milliliter(s)". And in the following respective Examples starting from an acylamido compound (IV), the production of the corresponding thioacylamido compound (III) was confirmed by thin layer chromatography.

REFERENCE 1

β-Methylsulfonylethyl 7-phenylacetamido-3-desacetoxycephalosporanate (13 parts) and pyridine (2.4 parts) were dissolved in dichloromethane (150 volume parts). At room temperature, phosphorus pentasulfide (15 parts) was added to the solution and the mixture was stirred for 5 hours.

The resultant insolubles were filtered off and the solution was washed with water, dried and concentrated. The resultant residue was chromatographed on silica gel by eluting with a mixture of dichloromethane and ether (1:4) to afford β-methylsulfonylethyl 7-phenylthioacetamido-3-desacetoxycephalosporanate (9.2 parts). Pale yellow needles (recrystallized from ethylalcohol). Melting point: 142°-144° C.

REFERENCE 2

Phosphorus pentachloride (6.5 parts) was suspended in dichloromethane (45 volume part), followed by the addition of pyridine (12 parts). The mixture was cooled to $-10°$ C and β-methylsulfonylethyl 7-phenylacetamido-3-desacetoxycephalosporanate (4.38 parts) was added. After the mixture was stirred for 2 hours at the same temperature, hydrogen sulfide was bubbled through the mixture at $-5°$ to $-10°$ C for 3 hours.

The dichloromethane solutions was poured into ice-water, and the organic layer was washed with water, dried and concentrated. The procedure yields β-methylsulfonylethyl 7-phenylthioacetamido-3-desacetoxycephalosporanate (4.26 parts). In IR and NMR spectra, the above product was in agreement with the product obtained in Reference 1.

REFERENCE 3

In dichloromethane (2000 volume parts) was suspended phosphorous pentachloride (312 parts), and to the suspension was added pyridine (240 parts) under cooling at 0° to $-5°$ C and stirring, followed by adding a solution of β-methylsulfonylethyl 7-phenylacetamido-3-desacetoxycephalosporanate (438 parts) dissolved in dichloromethane (2800 volume parts) over 30 minutes at the same temperature. The mixture was stirred for 1.5 hours at 0° to $-5°$ C, and to the reaction mixture was added dimethyl dithiophosphate (640 parts) while keeping the reaction temperature under 0° C, followed by stirring for 3 hours. The reaction mixture was filtered to collect the precipitates, which were washed with dichloromethane to give the crystals (461 parts) of an adduct consisting of β-methylsulfonylethyl 7-phenylthioacetamido-3-desacetoxycephalosporanate, pyridine and hydrogen chloride (1:1:1). Melting point: 129° to 137° C (decomp.).

EXAMPLE 1

1. In dichloromethane (5 volume parts) was dissolved β-methylsulfonylethyl 7-phenylthioacetamido-3-desacetoxycephalosporanate (0.454 part) and to the solution, under cooling with ice, methanol (1 volume part) and 27% ethanolic hydrochloric acid (0.35 volume part) were added.

With stirring to the resultant, N-bromosuccinimide (0.196 part) was added, and the whole mixture was stirred for 1 hour. The separated crystals were recovered by filtration, washed with dichloromethane and then dried.

The procedure yielded β-methylsulfonylethyl 7-amino-3-desacetoxycephalosporanate hydrochloride (0.278 part), the infrared spectrum of which was in complete agreement with that of an authentic sample obtained by a different route of synthesis.

2. In the above procedure, the N-bromosuccinimide was replaced with t-butyl hypochlorite (0.125 volume part) or chlorine (0.094 part) to obtain β-methylsulfonylethyl 7-amino-3-desacetoxycephalosporanate hydrochloride. The infrared spectrum of the product was in complete agreement with that of an authentic sample.

EXAMPLE 2

To dichloromethane (5 volume parts) were added pyridine (0.3 volume part) and thionyl chloride (0.1 volume part) in the order mentioned. The mixture was cooled to $-15°$ C and the plenum air of the reaction system was purged with nitrogen gas. Under stirring, to the mixture β-methylsulfonylethyl 7-phenylthioacetamido-3-desacetoxycephalosporanate (0.454 part) was added, followed by stirring for 30 minutes. To this reaction mixture was added methanol (8 volume parts) and, after stirring for 30 minutes, hydrochloric acid (0.2 volume part) was then added. The whole mixture was further stirred for 20 minutes, after which time it was concentrated and the resultant residue was diluted with water (10 volume parts). The mixture was then filtered and the filtrate was adjusted to pH 7.5 with sodium bicarbonate and extracted with dichloromethane (20 volume parts).

The extract was dried over anhydrous sodium sulfate and concentrated under reduced pressure. The residue was crystallized from dichloromethane-ether. The procedure yielded β-methylsulfonylethyl 7-amino-3-desacetoxycephalosporanate (0.176 part). Melting point: 122° C. IR(KBr disc): 3410, 3350, 1770, 1724, 1634 cm$^{-1}$.

EXAMPLE 3

In 1,2-dichloroethane (57 volume parts) was suspended an adduct consisting of β-methylsulfonylethyl 7-phenylthioacetamido-3-desacetoxycephalosporanate, pyridine and hydrogen chloride (5.70 parts) and to the suspension, under cooling with ice 10% methanolic hydrochloric acid (5 volume parts) was added. Then, to the resultant carbon tetrachloride (6.3 volume parts) containing chlorine (0.746 part) was added over a period of 90 minutes, after which time the mixture was further stirred for 60 minutes. The resultant crystals were recovered by filtration, washed with dichloroethane and dried. The procedure yielded β-methylsulfonylethyl 7-amino-3-desacetoxycephalosporanate hydrochloride (2.86 parts). The infrared spectrum of the product was in complete agreement with that of an authentic sample.

EXAMPLE 4

In toluene (60 volume parts) was suspended an adduct consisting of β-methylsulfonylethyl-7-phenylthioacetamido-3-desacetoxycephalosporanate, pyridine and hydrogen chloride (5.70 parts) and to the suspension under cooling with ice, 10% methanolic hydrochloric acid (20 volume parts) was added, followed by the addition of manganese dioxide powder (1.16 parts). The mixture was stirred for 60 minutes and the resultant crystals were recovered by filtration, washed with dichloromethane and dried. The procedure yielded β-methylsulfonylethyl 7-amino-3-desacetoxycephalosporanate hydrochloride (2.84 parts). The infrared spectrum of the product was in complete agreement with that of an authentic sample.

EXAMPLE 5

In a mixture of 1,2-dichloroethane (40 volume parts) and 10% methanolic hydrochloric acid (6 volume parts) was suspended an adduct consisting of β-methylsulfonylethyl 7-phenylthioacetamido-3-desacetoxycephalosporanate, pyridine and hydrogen chloride (5.70 parts) and to the suspension, under cooling with ice and stirring, N-chlorosuccinimide (1.33 parts) was added over a period of 30 minutes. The mixture was further stirred under cooling with ice for 2 hours, after which time the precipitate was recovered by filtration. The precipitate was recrystallized from methanoltoluene to obtain β-methylsulfonylethyl 7-amino-3-desacetoxycephalosporonate hydrochloride (3.0 parts). The infrared spectrum of the product was in complete agreement with that of an authentic sample. β-Methylsulfonylethyl 7-phenylacetamido-3-desacetoxycephalosporanate (i.e. reconversion product) was not detected in the resultant mother liquior nor crude precipitate obtained by thin layer chromatography and IR spectrum.

EXAMPLE 6

In a mixture of 1,2-dichloroethane (37 volume parts) and 10% methanolic hydrochloric acid was suspended an adduct consisting of β-methylsulfonylethyl 7-phenylthioacetamido-3-desacetoxycephalosporanate, pyridine and hydrogen chloride (5.70 parts) and to the suspension, under cooling at −10° C, a solution of bromine (1.7 parts) in 1,2-dichloroethane (5 volume parts) was added dropwise over a period of 15 minutes. The mixture was further stirred at −10° C for 2 hours, after which time the resulting precipitate was recovered by filtration.

The precipitate was then recrystallized from methanoltoluene to obtain β-methylsulfonylethyl 7-amino-3-desacetoxycephalosporanate hydrochloride (3.1 parts). The infrared spectrum of the product was in complete agreement with that of an authentic sample.

EXAMPLE 7

In dichloromethane (5 volume parts) was suspended 7-phenylthioacetamido-3-desacetoxycephalosporanic acid (0.348 part), and to the suspension, under cooling with ice, methanol (1.0 volume part) and 27% ethanolic hydrochloric acid (0.5 volume part) were added. Thereafter, under stirring, sulfuryl chloride (0.1 volume part) was added, followed by further stirring for 5 minutes. Then, water (2 volume parts) was added and the reaction mixture was adjusted to pH 3.8 with concentrated aqueous ammonia and stirred at 0° C for further 30 minutes. The resultant precipitate was recovered by filtration, washed with 75% methanol and dichloromethane in this order and dried.

The procedure yielded 7-amino-3-desacetoxycephalosporanic acid (0.180 part), the infrared spectrum of which was in complete agreement with that of an authentic sample.

EXAMPLE 8

In dichloromethane (10 volume parts) was suspended 7-phenylthioacetamido-3-desacetoxycephalosporanic acid (0.348 part), followed by the addition of N,N-dimethylaniline (0.2 volume part). Under cooling with ice and stirring, to the resultant N-chlorosuccinimide (0.146 part) was added and the mixture was further stirred for 20 minutes, after which time to the resulting mixture a mixture of methanol (5 volume parts) and concentrated hydrochloric acid (0.5 volume part) was added. The whole mixture was stirred for 20 minutes. The reaction mixture was adjusted to pH 3.8 with concentrated aqueous ammonia and stirred under cooling with ice for further 20 minutes. The resultant precipitate was recovered by filtration, washed with 75% methanol, methanol and dichloromethane in the order mentioned and finally dried. The procedure yielded 7-amino-3-desacetoxycephalosporanic acid (0.173 part), the infrared spectrum of which was in complete agreement with that of an authentic sample.

EXAMPLE 9

In dichloromethane (40 volume parts) was suspended 7-phenylacetamido-3-desacetoxycephalosporanic acid (1.66 parts) and to the suspension, under cooling with ice and stirring, triethylamine (0.7 volume part) was added. The mixture was stirred for 5 minutes, after which time dimethyldichlorosilane (0.35 volume part) was added. The mixture was stirred at room temperature for 40 minutes. The mixture was then chilled to −20° C and to the mixture phosphorus pentachloride (1.40 parts) was added. The whole mixture was then stirred at a constant temperature of −20° to −10° C for 2 hours. Thereafter, thioacetamide (1.0 part) was added, followed by stirring at −15° to −10° C for 1 hour. The mixture was chilled to −20° C and, then, to the resultant a mixture of methanol (10 volume parts) and 27% ethanolic hydrochloric acid (1 volume part) was added. The whole mixture was further stirred for 10 minutes, after which time N-chlorosuccinimide (1.3 parts) was added. The mixture was stirred for 1 hour, after which time the reaction mixture was filtered. To the filtrate was added water (7 volume parts) and, under cooling with ice and stirring, the mixture was adjusted to pH 3.8 with concentrated aqueous ammonia. The resultant was stirred under cooling with ice for 1 hour and the resultant precipitate was recovered by filtration, washed with dichloromethane and 75% methanol in this order and dried. The procedure yielded 7-amino-3-desacetoxycephalosporanic acid (0.91 part). The infrared spectrum of the product was in complete agreement with that of an authentic sample.

EXAMPLE 10

In dichloromethane (40 volume parts) was suspended N-(p-t-butylbenzoyl)-cephalosporin C (2.88 parts) and to the suspension, under cooling with ice and stirring, triethylamine (1.4 volume parts) was added. The mixture was stirred for 5 minutes, after which time to the resultant N,N-dimethylaniline (1.95 volume parts) and dimethyldichlorosilane (0.7 volume part) were added in this order, followed by stirring for 10 minutes. Then, the mixture was stirred at room temperature for 1 hour and, then, chilled to −20° C. Following the addition of phosphorus pentachloride (1.4 parts), the whole mixture was stirred for 2.5 hours, followed by the addition of thioacetamide (0.8 part). The mixture was stirred for 30 minutes. Then, following the addition of N,N-dimethylaniline (1.0 volume part), the mixture was further stirred for 30 minutes. Then, to the resultant N-chlorosuccinimide (1.3 parts) was added over a period of 20 minutes, after which time the resultant mixture was chilled to −20° C and to the mixture a mixture of methanol (10 volume parts) and 27% ethanolic hydrochloric acid (4 volume parts) was added. The mixture was stirred for 2 hours. Then, to the resultant water (7 volume parts) was added at 0° to 5° C over a period of 5 minutes and the mixture was adjusted to pH 3.5 with concentrated aqueous ammonia, followed by stirring for an additional 30 minutes. The resultant precipitate was recovered by filtration, washed well with dichloromethane and methanol in this order and dried. The procedure yielded 7-aminocephalosporanic acid (1.01 part), the infrared spectrum of which was in complete agreement with that of an authentic sample.

EXAMPLE 11

Under stirring, N-phthaloyl-cephalosporin C (2.73 parts) was added to a mixture of dichloromethane (30 volume parts) and N,N-dimethylaniline (4.0 volume parts). The whole mixture was chilled to −20° C and, with stirring to the mixture, phosphorus trichloride (1.0 volume part) was added. Then, the mixture was stirred for 20 minutes, followed by addition of phosphorus pentachloride (1.2 parts) at −20° C.

The mixture was stirred for further 1 hour, after which time to the resultant thioacetamide (0.9 part) was added. The mixture was further stirred for 1 hour and, then, to the mixture N-chlorosuccinimide (1.61 parts) was added. The resultant mixture was stirred for 50 minutes and chilled to −20° C. Then, to the mixture a mixture of methanol (10 volume parts) and 27% ethanolic hydrochloric acid (2 volume parts) was added. After 10 minutes to the resultant, water (7 volume parts) was added and the whole mixture was stirred for 10 minutes. The reaction mixture was adjusted to pH 3,5 with concentrated aqueous ammonia and stirred at 0° C for 1 hour. The resultant precipitate was recovered by filtration, washed with dichloromethane, methanol and 75% methanol in this order and dried. The procedure yielded 7-aminocephalosporanic acid (0.99 part), the infrared spectrum of which was in complete agreement with that of an authentic sample.

EXAMPLE 12

N-phthaloyl-cephalosporin C (2.80 parts) was suspended in dichloromethane (40 volume parts) at 0° C and to the suspension, under stirring, triethylamine (1.44 volume parts) was added. After 10 minutes to the resultant, N,N-dimethylaniline (1.95 volume parts) and dimethyldichlorosilane (0.63 volume parts) were added in this order and the mixture was stirred for 1 hour, after which time the resultant mixture was chilled to −20° C.

Following the addition of phosphorus pentachloride (1.40 parts), the mixture was stirred for 1 hour and, then to the mixture, N,N-dimethylaniline (1.40 volume parts) was added, followed further by the addition of thioacetamide (1.0 part). The mixture was stirred for 1 hour. Then, at −20° C, N-chlorosuccinimide (1.8 parts) was added and the mixture was stirred for 30 minutes. Following the addition of a mixture of methanol (10 volume parts) and 27% ethanolic hydrochloric acid (3 volume parts), the mixture was stirred for 20 minutes, after which time water (7 volume parts) was added. The whole mixture was stirred for 10 minutes. The resultant mixture was adjusted to pH 3.5 with concentrated aqueous ammonia and stirred at 0° C for 1 hour. The resultant precipitate was recovered by filtration, washed well with dichloromethane and methanol, and dried. The procedure yielded 7-aminocephalosporanic acid (1.04 parts), the infrared spectrum of which was in complete agreement with that of an authentic sample.

EXAMPLE 13

In dichloromethane (40 volume parts) was dissolved dimethylaniline (5.32 volume parts) and, then, 7-(5-p-t-butylbenzoylamido-5-carboxyvaleramido)-3-(2-morpholinoethoxy)iminomethyl-3-cephem-4-carboxylic acid (4.62 parts) was suspended in the solution. The suspension was chilled to −10° C and, under stirring to the suspension, phosphorus trichloride (1.575 volume parts) was added. The mixture was further stirred at −10° C for 1 hour, after which time the resultant mixture was chilled to −20° C. Then, to the resultant phosphorus pentachloride (2.9 parts) was added, followed by stirring at −15° to −20° C for 2 hours. Thereafter to the mixture, thioacetamide (2.25 parts) was added and the whole mixture was stirred for 1 hour. Then, methanol (20 volume parts) was slowly added dropwise at −20° C and the mixture was stirred for 30 minutes, after which time to the resultant N-chlorosuccinimide (4.0 parts) was added. The mixture was stirred for 1 hour. After the addition of water (20 volume parts), the reaction mixture was extracted three times with each of water (20 volume parts). The extracts were pooled, concentrated and chromatographed on a column of XAD-2 type resin with water as the developer. The eluate was freeze-dried to obtain 7-amino-3-(2-morpholinoethoxy)iminomethyl-3-cephem-4-carboxylic acid (2.26 parts).

IR(KBr): 1788 cm$^{-1}$.

NMR(D$_2$O): δ 3.2–4.9(m, 14H), 5.20(d, J=5Hz, 6-H), 5.56 (d, J=5Hz), 8.57(s, —CH=NO—).

EXAMPLE 14

In dichloromethane (25 volume parts) was suspended potassium salt of benzyl-penicillin (6.0 parts), and to the suspension, under stirring at room temperature, N,N-dimethylaniline (5.2 volume parts) and dichlorodimethylsilane (1.6 volume parts) were added in this order. The mixture was stirred for 30 minutes. Then, the mixture was chilled to −30° C and to the mixture phosphorus pentachloride (3.6 parts) was added, followed by stirring at −30° C for 2 hours. Then to the resultant, thioacetamide (1.5 parts) was added and the whole mixture was stirred at −30° to −25° C for 1.5 hours. Then, under stirring at −30° C to the mixture, methanol (20 volume parts) was added dropwise at a temperature not exceeding −25° C and, then, N-chlorosuccinimide (2.5 parts) was added.

The mixture was stirred for 20 minutes. Under stirring at −30° C, water (5 volume parts) was added and, then to the resultant, concentrated aqueous ammonia (20 volume parts) was slowly added drop by drop. In an ice bath, the reaction mixture was adjusted to pH 4.1 with aqueous ammonia and stirred for 1 hour. The resultant precipitate was recovered by filtration, washed with 50% methanol and dichloromethane, and dried. The procedure yielded 6-aminopenicillanic acid (2.1 parts). The IR spectrum of this product was in agreement with that of an authentic sample.

EXAMPLE 15

1. In a 10% aqueous solution of dipotassiumphosphate (200 volume parts) was dissolved sodium salt of cephalosporin C (20 parts), and the solution was adjusted to pH 9.1 with tribasic potassium phosphate. To the solution were added acetone (80 volume parts) and then a solution of N-carboethoxyphthalimide (12 parts) in acetone (120 volume parts) under stirring at 22° C, followed by stirring at the same temperature for further 1 hour, during which time pH value of the reaction system was kept to 9.1 with tribasic potassium phosphate. The resultant reaction mixture was adjusted to pH 7 with phosphoric acid, and then acetone was distilled off under reduced pressure. The residue was washed with ethyl acetate, adjusted to pH 2.0 with phosphoric acid and then extracted with ethyl acetate (200 volume parts). To the ethyl acetate layer was added water (200 volume parts), and the mixture was adjusted to pH 7.0 with sodium bicarbonate under stirring. The water layer was separated out, and small amount of ethyl acetate remaining in the layer was distilled off under reduced pressure. To the resultant water layer was added 1-methyl-1H-tetrazol-5-thiol(5.0 parts), and the mixture was adjusted to pH 5.0 with dipotassium phosphate, followed by stirring and heating at 65° C on a steam-bath for 4 hours. After cooling the reaction mixture was adjusted to pH 2.0 with phosphoric acid and extracted with ethyl acetate (200 volume parts). The ethyl acetate layer was dried on sodium sulfate and concentrated. To the residue was added toluene to give powdery product. The product was recovered by filtration, dried and then dissolved in ethyl acetate. The resultant insolubles were filtered off, and the filtrate was concentrated under reduced pressure. To the residue was added toluene to give powdery product. The same purification procedure is conducted once more to yield 7-(D-5-phthalimido-5-carboxyvaleramido)-3-(1-methyltetrazol-5-yl)thiomethyl-3-cephem-4-carboxylic acid (13.0 parts).

IR(KBr disc): 1778, 1717 cm$^{-1}$.

NMR(in d$_6$-DMSO): δ 1.3–2.5(m, 6H), 3.63(ABq, 2—CH$_2$), 3.93 (s, tetrazol —CH$_3$), 4.30(3—CH$_2$S—), 4.73(t, =N—CH—COO), 5.01(d, J=5Hz, 6—H), 5.62(q, J=5 and 8 Hz, 7—H), 7.85 (s.

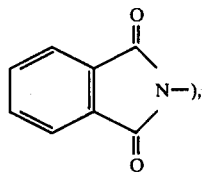

7.78(d, J=8Hz).

2. In dry dichloromethane (25 volume parts) was suspended 7-(D-5-phthalimido-5-carboxyvaleramido)-3-(1-methyltetrazol-5-yl)thiomethyl-3-cephem-4-carboxylic acid (3.0 parts), and to the suspension were added triethylamine (1.4 volume parts), dimethylaniline (5.0 volume parts) and dimethyldichlorosilane (1.5 volume parts) in this order under stirring at room temperature (20° C). The mixture was stirred at 28° C for 1 hour and then chilled to −25° C, and to the resultant was added phosphorus pentachloride (1.8 parts), followed by stirring at −20° to −15° C for 1.5 hours.

To the resultant was added thioacetamide (1.0 part) and stirred at −10° to −15° C for 1 hour, followed by addition of N-chlorosuccinimide (1.5 parts) and stirring for further 15 minutes. To the resultant were added at −15° C methanol (20 volume parts) and water (10 volume parts), and the mixture was adjusted to pH 3.3 with ammonium bicarbonate, followed by cooling with ice for 1 hour. The resultant crystals were recovered by filtration, washed with 50% methanol, methanol and dichloromethane in this order and dried to give 7-amino-3-(1-methyltetrazol-5-yl)thiomethyl-3-cephem-4-carboxylic acid (1.2 parts).

IR (KBr disc): 1795 cm$^{-1}$.

NMR(in D$_2$O and NaHCO$_3$): δ 3.61 and 3.98(ABq, J=18Hz, 2—CH$_2$), 4.12(s, tetrazol —CH$_3$), 5.21 (d, J=4.5 Hz, 6—H), 5.60 (d, J=4.5Hz, 7—H).

In the above procedure, N-chlorosuccinimide was replaced with bromine (2.1 parts) or sulfuryl chloride (1.4 volume parts) to obtain 1.2 parts or 1.1 parts of the same product respectively.

EXAMPLE 16

According to the similar procedure to that of Example 15-(2), from the following 7-substituted amino-3-cephem-4-carboxylic acid derivatives (i.e. starting compounds) were obtained the corresponding 7-amino-3-cephem-4-carboxylic acid derivatives (i.e. products) respectively, which are described in the following table;

| Ex. | Starting compound (amount used) | Product (yield) | IR: cm$^{-1}$ (KBr disc) | NMR: δ ppm (in D$_2$O + NaHCO$_3$) |
|---|---|---|---|---|
| 16-(1) | 7-(D-5-phthalimido-5-carboxy-valeramido)-3-(5-methyl-1,3,4-thiadiazol-2-yl)thiomethyl-3-cephem-4-carboxylic acid (3.14 parts) | 7-amino-3-(5-methyl-1,3,4-thiadiazol-2-yl)thiomethyl-3-cephem-4-carboxylic acid (1.1 parts) | 1795 | 2.87(s,thiadiazol -CH$_3$), 3.53 and 3.95 (ABq, J=18Hz,2-CH$_2$), 4.10 and 4.46(ABq, J=13Hz,3-CH$_2$), 5.17(d,J=4.5Hz,6-H) 5.58(d,J=4.5Hz,7-H) |
| 16-(2) | 7-(D-5-phthalimido-5-carboxy-valeramido)-3-(5-methyl-1,3,4-oxadiazol-2-yl)thiomethyl-3-cephem-4-carboxylic acid (3.0 parts) | 7-amino-3-(5-methyl-1,3,4-oxadiazol-2-yl)thiomethyl-3-cephem-4-carboxylic acid (1.4 parts) | 1798 | 2.74(s,oxadiazol -CH$_3$), 3.58 and 4.02(ABq,J=18Hz,2-CH$_2$), 4.10 and 4.68(ABq, J=14Hz,3-CH$_2$), 5.22(d,J=5Hz,6-H) 5.62(d,J=5Hz,7-H) |
| 16-(3) | 7-(D-5-phthalimido-5-carboxy-valeramido)-3-(1,3,4-thiadiazol-2-yl)thiomethyl-3-cephem-4-carboxylic acid (3.0 parts) | 7-amino-3-(1,3,4-thiadiazol-3-yl)thiomethyl-3-cephem-4-carboxylic acid (1.2 parts) | 1798 | 3.57 and 3.96(ABq,J=18Hz,2-CH$_2$), 4.17 and 4.69(ABq,J=14Hz,3-CH$_2$), 5.18 (d,J=5Hz,6-H),5.58 (d,J=5Hz,7-H),9.58 (s,thiadiazol-H) |

EXAMPLE 17

1. In a mixture of water (500 volume parts) and acetone (150 volume parts) was dissolved monosodium salt of cephalosporin C (47.4 parts), and the solution was adjusted to pH 9.0 with sodium carbonate.

To the solution was added dropwise isobornyl chlorocarbonate (43.3 parts) over a period of 1.5 hours under cooling at 3° to 4° C and under keeping pH value of the reaction system to 9.0 with sodium carbonate. After stirring at the same temperature for further 1.5 hours, the reaction mixture was adjusted to pH 7.0 with phosphoric acid, and then acetone was distilled off under reduced pressure. The resultant was washed twice with each of ethyl acetate (400 volume parts), and the water layer was separated out.

The water layer was adjusted to pH 2.5 with phosphoric acid and then extracted three times with (600 volume parts) each of ethyl acetate. The ethyl acetate layer was dried over sodium sulfate and then concentrated to dryness under reduced pressure to give N-isobornyloxycarbonyl-cephalosporine C (55.4 parts).

IR(KBr disc): 1790, 1720 cm$^{-1}$.

2. In phosphoric acid buffer solution of pH 6.4 (60 volume parts) were dissolved N-isobornyloxycarbonyl-cephalosporin C (5.95 parts), 1-methyl-1H-tetrazol-5-thiol(1.16 parts) and sodium bicarbonate (2.52 parts), and the solution was adjusted to pH 6.4 with sodium bicarbonate. The solution was heated at 60° C for 14 hours in nitrogen gas stream under stirring. After cooling, the reaction mixture was adjusted to pH 2.5 with 10% phosphoric acid and the resultant was extracted twice with each of ethyl acetate (80 volume parts). The ethyl acetate layer was dried over sodium sulfate and concentrated to dryness under reduced pressure. The procedure yielded 7-(D-5-isobornyloxycarbonylamido-5-carboxyvaleramido)-3-(1-methyltetrazol-5-yl)thiomethyl-3-cephem-4-carboxylic acid (3.28 parts).

3. According to a similar procedure to that of Example 15-(2), from 7-(D-5-isobornyloxycarbonylamido-5-carboxyvaleramido)-3-(1-methyltetrazol-5-yl)thiomethyl-3-cephem-4-carboxylic acid (3.25 parts) was obtained 7-amino-3-(1-methyltetrazol-5-yl)thiomethyl-3-cephem-4-carboxylic acid (1.42 parts).

This product is in complete agreement with the product obtained in Example 15 in IR and NMR spectra.

EXAMPLE 18

1. According to a similar procedure to that of Example 17-(1) except that isobornyl chlorocarbonate was replaced with p-(t-butyl)benzoylchloride (27.9 parts), and the reaction was carried out at 15° C, N-[p-(t-butyl)benzoyl] cephalosporin C was obtained from monosodium salt of cephalosporin C.

IR(KBr disc): 1778, 1730, 1708 cm$^{-1}$.

NMR(in d$_6$-DMSO): δ 1.28(9H), 1.5–1.9(4H), 2.01(3H),2.10 –2.35(2H), 3.36 and 3.61(2H,ABq), 4.37(1H), 4.68 and 4.99(2H,ABq), 5.06(1H), 5.67(1H), 7.46 and 7.82(4H, ABq), 8.41(1H), 8.79(1H).

2. According to a similar procedure to that of Example 17-(2), from N-[p-(t-butyl)benzoyl]cephalosporin C (5.75 parts) was obtained 7-(D-5-t-butylbenzoylamido-5-carboxyvaleramido)-3-(1-methyltetrazol-5-yl)thiomethyl-3-cephem-4-carboxylic acid (3.82 parts).

3. In dry dichloromethane (20 volume parts) was suspended 7-(D-5-t-butylbenzoylamido-5-carboxyvaleramido)-3-(1-methyltetrazol-5-yl)thiomethyl-3-cephem-4-carboxylic acid (3.16 parts), and to the suspension were added triethylamine (1.2 volume parts), dimethylaniline (4.0 volume parts) and dimethyldichlorosilane (1.0 volume part) in this order, followed by stirring at 30° C. To the reaction mixture which was chilled at −25° C, was added phosphorus pentachloride (1.6 parts) and the whole mixture was stirred for 1.5 hours. To the resultant was added thioacetamide (1.2 parts) and, the mixture was stirred at −10° to −15° C for 1 hour. After which time, to the reaction mixture was added N-chlorosuccinimide (1.2 parts) under stirring for 15 minutes, and to the resultant were added at −15° C methanol (20 volume parts) and water (10 volume parts). The whole mixture was adjusted to pH 3.3 with ammonium bicarbonate and then stirred under cooling with ice for 1 hour. The resultant crystals were recovered by filtration, washed with 50% methanol, methanol and dichloromethane in this order and dried to give 7-amino-3-(1-methyltetrazol-5-yl)thiomethyl-3-cephem-4-carboxylic acid (1.3 parts). This product is in complete agreement with the product obtained in Example 15 in IR and NMR spectra.

EXAMPLE 19

1. According to a similar procedure to that of Example 17-(1) except that isobornyl chlorocarbonate was replaced with p-(t-outyl)benzenesulfonylchloride (29.4 parts) and the reaction was carried out at room temperature (about 20° C), N,-[p-(t-butyl)benzenesulfonyl]-cephalosporin C was obtained from monosodium salt of cephalosporin C.

IR(KBr disc): 1770, 1728, 1710, 1660 cm$^{-1}$.

NMR (in d$_6$-DMSO): δ 1.29 (9H), 2.01(3H), 3.40 and 3.64 (2H, ABq), 4.70 and 5.02(2H, ABq), 5.06(1H,d), 5.64 (1H,q), 7.50 and 7.68(4H, ABq), 7.94(1H,d), 8.72(1H,d).

2. According to a similar procedure to that of Example 17-(2), 7-(D-5-t-butylbenzenesulfonamido-5-carboxyvaleramido)-3-(1-methyltetrazol-5-yl)thiomethyl-3-cephem-4-carboxylic acid (3.67 parts) was obtained from N-[p-(t-butyl)benzenesulfonyl])cephalosporin C (6.11 parts).

IR(KBr disc): 1783, 1731, 1158 cm$^{-1}$.

NMR (in d$_6$-DMSO): 1.27(s, 9H), 1.51(4H), 2.08(2H), 3.66 (2H,2—CH$_2$), 3.92(s,3H, tetrazol —CH$_3$), 4.28(2H, 3—CH$_2$), 5.02(d, J=5Hz,6—H), 5.60(dd, J=5 and 8Hz, 7—H), 7.51 and 7.69(4H, ABq), 7.94(d, J=8Hz, —NHSO$_2$—), 8.74(d, J=8Hz, —CONH—).

3. In dry dichloromethane (30 volume parts) was suspended 7-(D-5-p-t-butylbenzenesulfonamido-5-carboxyvaleramido)-3-(1-methyltetrazol-5-yl)thiomethyl-3-cephem-4-carboxylic acid (3.43 parts), and to the suspension, under stirring at room temperature (20° C), were added triethylamine (1.4 volume parts), dimethylaniline (5.0 volume parts) and dimethyldichlorosilane (1.5 volume parts) in this order, followed by stirring at 28° C for 1 hour. To the reaction mixture, which was chilled at −25° C, was added phosphorus pentachloride (1.4 parts) and the whole mixture was stirred at −10° to −15° C for 1.5 hours. After which time, thioacetamide (1.0 part) was added and to the reaction mixture was added N-chlorosuccinimide (1.5 parts) under stirring for 15 minutes, and to the resultant were added at −15° C methanol (20 volume parts) and water (10 volume parts). The whole mixture was adjusted to pH 3.3 with ammonium bicarbonate and then stirred under cooling with ice for 1 hour. The resultant crystals were recovered by filtration, washed with 50% methanol, methanol and dichloromethane in this order and dried to give 7-amino-3-(1-methyltetrazol-5-yl)thiomethyl-3-cephem-4-carboxylic acid (1.3 parts). This product was in complete agreement with the product obtained in Example 15 in IR and NMR spectra.

EXAMPLE 20

1. A solution of N-phthaloylcephalosporin C (5.46 parts), 2-(β-hydroxyethylthio)-5-mercapto-1,3,4-thiadiazole(1.94 parts) and sodium bicarbonate (2.20 parts) in water (60 volume parts) was heated at 65° C for 4 hours. The reaction mixture was adjusted to pH 5.0 with 4N-hydrochloric acid, followed by washing with ethyl acetate.

To the resultant were added ethyl acetate (30 volume parts) and tetrahydrofuran (20 volume parts), and the mixture was adjusted to pH 2.0 with 4N-hydrochloric acid.

The resulting organic layer was washed with a saturated aqueous solution of sodium chloride, dried over magnesium sulfate and subjected to evaporation of the solvent under reduced pressure. To the resultant residue ethyl acetate (20 volume parts) and ether (30 volume parts) were added to give powdery substance. The resultant powdery substance was collected by filtration to give 7-(D-5-phthalimido-5-carboxyvaleramido)-3-[5-(β-hydroxyethylthio)-1,3,4-thiadiazol-2-yl]thiomethyl-3-cephem-4-carboxylic acid (4.45 parts).

IR(KBr disc): (cm$^{-1}$), 1777, 1730, 1715.

NMR(in d$_6$-DMSO): δ 1.30–2.40(m,6H), 3.20–3.80(m,6H), 4.36 (AB pattern, 2H,J=13cps), 4.75(t,1H,J=8cps), 5.05(d, 1H,J=5cps), 5.64(q,1H,J=5, 9cps), 7.88(s,4H), 8.80 (d,1H,J=9cps).

2. In dry dichloromethane (25 volume parts) was suspended 7-(D-5-phthalimido-5-carboxyvaleramido)-3-[5-(β-hydroxyethylthio)-1,3,4-thiadiazol-2-yl]thiomethyl-3-cephem-4-carboxylic acid (2.8 parts), and to the suspension were added triethylamine (1.4 volume parts), dimethylaniline (5.0 volume parts) and dimethyldichlorosilane (1.5 volume parts) in this order under cooling with ice water. Then the mixture was stirred at 28° C for 2 hours and then chilled to −30° C, and to the resultant was added phosphorus pentachloride (1.8 parts), followed by stirring at −20° to −15° C for 1 hour.

To the resultant was added thioacetamide (1.0 part) and stirred at −10° to −15° C for 1 hour, followed by addition of N-chlorosuccinimide (1.6 parts) and stirred for further 15 minutes. To the resultant were added at −15° C methanol (20 volume parts) and water (10 volume parts), and the mixture was adjusted to pH 3.3 with ammonium bicarbonate, followed by cooling with ice for 1 hour. The resultant crystals were recovered by filtration, washed with 50% methanol, methanol and dichloromethane in this order and dried to give 7-amino-3-[5-(β-hydroxyethylthio)-1,3,4-thiadiazol-2-yl]thiomethyl-3-cephem-4-carboxylic acid (1.2 parts).

IR(KBr disc): 1800 cm$^{-1}$.

NMR(in D$_2$O and NaHCO$_3$): 3.54(t,J=6Hz,SCH$_2$CH$_2$—), 3.54 & 3.75 (q, J=16Hz, 2—CH$_2$—), 3.91(t,J=6Hz,CH$_2$OH), 4.07 & 4.38 (q, J=13Hz,3—CH$_2$), 5.05(d,J=5Hz,6—H), 5.45(d, J=5Hz, 7—H).

EXAMPLE 21

According to the similar procedure to that of Example 20-(2), from the following 7-substituted amino-3-cephem-4-carboxylic acid derivatives (i.e. starting compounds) were obtained the corresponding 7-amino-3-cephem-4-carboxylic acid derivatives (i.e. products) respectively, which are described in the following table;

| Ex. | Starting compound (amount used) | Product (yield) | IR:cm$^{-1}$ (KBr disc) | NMR: δ ppm |
|---|---|---|---|---|
| 21-(1) | 7-(D-5-phthalimido-5-carboxyvaleramido)-3-(5-carboxymethyl-1,3,4-thiadiazol-2-yl)thiomethyl-3-cephem-4-carboxylic acid (3.3 parts) | 7-amino-3-(5-carboxymethyl-1,3,4-thiadiazol-2-yl)thiomethyl-3-cephem-4-carboxylic acid (1.3 parts) | 1800 | (100 MHz, in NaHCO$_3$-D$_2$O); 3.60,3.98(ABq,J=18Hz, 2-CH$_2$),3.98(s,CH$_2$COO), 4.23, 4.67(ABq,J=14Hz, 3-CH$_2$),5.25(d,J=5Hz, 6-H),5.64(d,J=5Hz,7-H) |
| 21-(2) | 7-(D-5-phthalimido-5-carboxyvaleramido)-3-[(5-N,N-dimethylcarbamoylmethyl)-1,3,4-thiadiazol-2-yl]-thiomethyl-3-cephem-4-carboxylic acid (3.4 parts) | 7-amino-3-[(5-N,N-dimethylcarbamoylmethyl)-1,3,4-thiadiazol-2-yl]-thiomethyl-3-cephem-4-carboxylic acid (1.3 parts) | 1795 1642 | (60MHz, in NaHCO$_3$-D$_2$O); 3.00, 3.15(each s,N(CH$_3$)$_2$ ),3.36,3.78(ABq,J=17Hz, 2-CH$_2$),3.99,4.45(ABq, J=13Hz, 3-CH$_2$),4.10(s, -CH$_2$CO),5.06(d,J=5Hz, 6-H,5.44(d,J=5Hz,7-H) |

What we claim is:

1. A process for preparing a compound of the formula $H_2N$—A wherein A is a penicillin moiety represented by the formula

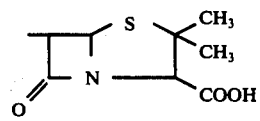

wherein the carboxy group is unprotected or protected by a conventional protecting group, or A is a cephalosporin moiety represented by the formula

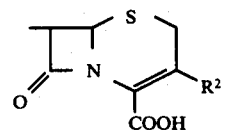

wherein the carboxy group is unprotected or protected by a conventional protecting group and R$^2$ is a group which does not take part in the reaction described below and is a member selected from the group consisting of 1. lower alkyl,
2. lower alkoxymethyl,
3. lower alkanoyloxymethyl,
4. a group represented by the formula

—CH$_2$SR$^3$ wherein R$^3$ is lower alkyl or a 5 or 6 membered nitrogen-containing heterocyclic group having 1 to 4 hetero atoms selected from the group consisting of nitrogen, oxygen and sulfur, the nitrogen being in the oxide or non-oxide form, which nitrogen-containing heterocyclic group is unsubstituted or substituted by (a) lower alkyl, (b) trifluoromethyl, (c) lower alkoxy, (d) halogen, (e) amino, (f) mercapto, (g) hydroxy, (h) carbamoyl, (i) carboxy, (j) lower alkyl substituted by hydroxy, mercapto, amino, morpholino, carboxy, sulfo, carbamoyl, alkoxycarbonyl having 2 to 13 carbon atoms, mono- or di- lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, (k) mercapto substituted by lower alkyl wherein the lower alkyl is unsubstituted or substituted by hydroxy, mercapto, amino, morpholino, carboxy, sulfo, carbamoyl, alkoxycarbonyl having 2 to 13 carbon atoms, mono- or di- lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, or (1) amino mono- or di- substituted by carboxy, carbamoyl, lower alkyl, alkoxycarbonyl having 2 to 13 carbon atoms, lower alkyl carbamoyl, or lower alkyl substituted by hydroxy, mercapto, amino, morpholino, carboxy, sulfo, carbamoyl, alkoxycarbonyl having 2 to 13 carbon atoms, mono- or di- lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, and
5. an iminomethyl group of the formula

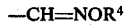

wherein $R^4$ is alkyl having 1 to 6 carbon atoms or cycloalkyl having up to 6 carbon atoms, which alkyl and cycloalkyl groups are unsubstituted or substituted by (a) allyl, (b) phenyl, (c) an unsubstituted 5 or 6 membered heterocyclic group having 1 or 2 hetero atoms selected from the group consisting of nitrogen, oxygen and sulfur, (d) carboxy or (e) pyridinium,
which comprises reacting a compound of the forumla

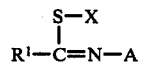

wherein A has the same meaning as above, $R^1$ is an organic residue derived from an acylamido group in the 6- position of a penicillin or the 7-position of a cephalosporin by eliminating the —CONH— moiety of the acylamido group, which organic residue is capable of combination with a thiocarbonyl group to form a thioacyl group, and X is chlorine or bromine,
with a solvolysis solvent selected from the group consisting of aliphatic alcohols having 1 to 4 carbon atoms, glycols having 2 to 4 carbon atoms, glycerine, acetic acid, propionic acid, methylmercaptan, ethylmercaptan and water 2. A process as claimed in claim 1, wherein the lower alkanoyloxymethyl is acetoxymethyl or propionyloxymethyl.
3. A process for preparing a compound of the formula

wherein A is a penicillin moiety represented by the formula

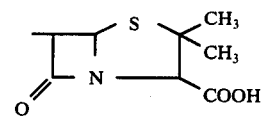

wherein the carboxy group is unprotected or protected by a conventional protecting group, or A is a cephalosporin moiety represented by the formula

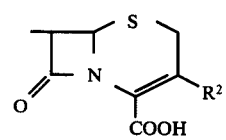

wherein the carboxy group is unprotected or protected by a conventional protecting group and $R^2$ is a group which does not take part in the reactions described below and is a member selected from the group consisting of
 1. lower alkyl,
 2. lower alkoxymethyl,
 3. lower alkanoyloxymethyl,
 4. a group represented by the formula

wherein $R^3$ is lower alkyl or a 5 or 6 membered nitrogen-containing heterocyclic group having 1 to 4 hetero atoms selected from the group consisting of nitrogen, oxygen and sulfur, the nitrogen being in the oxide or non-oxide form, which nitrogen-containing heterocyclic group is unsubstituted or substituted by (a) lower alkyl, (b) trifluoromethyl, (c) lower alkoxy, (d) halogen, (e) amino, (f) mercapto, (g) hydroxy, (h) carbamoyl (i) carboxy, (j) lower alkyl substituted by hydroxy, mercapto, amino, morpholino, carboxy, sulfo, carbamoyl, alkoxycarbonyl having 2 to 13 carbon atoms, mono- or di- lower alkyl carbamoyl alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, (k) mercapto substituted by lower alkyl wherein the lower alkyl is unsubstituted or substituted by hydroxy, mercapto, amino, morpholino, carboxy, sulfo, carbamoyl, alkoxycarbonyl having 2 to 13 carbon atoms, mono- or di- lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino or (1) amino monoor di- substituted by carboxy, carbamoyl, lower alkyl, alkoxycarbonyl having 2 to 13 carbon atoms, lower alkyl carbamoyl, or lower alkyl substituted by hydroxy, mercapto, amino, morpholino, carboxy, sulfo, carbamoyl, alkoxycarbonyl having 2 to 13 carbon atoms, mono- or di-lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, and 5. an iminomethyl group of the formula

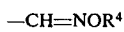

wherein R⁴ is alkyl having 1 to 6 carbon atoms or cycloalkyl having up to 6 carbon atoms, which alkyl and cycloalkyl groups are unsubstituted or substituted by (a) allyl, (b) phenyl (c) an unsubstituted 5 to 6 membered heterocyclic group having 1 or 2 hetero atoms selected from the group consisting of nitrogen, oxygen and sulfur, (d) carboxy or (e) pyridinium, which comprises chlorinating or bominating a compound of the formula

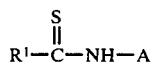

wherein R¹ is an organic residue derived from an acylamido group in the 6- position of a penicillin or the 7- position of a cephalosporin by eliminating the —CONH— moiety of the acylamido group, which organic residue is capable of combination with a thiocarbonyl group to form a thioacyl group, and A has the same meaning as above, to obtain a compound of the formula

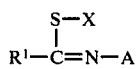

wherein X is chlorine or bromine, and R¹ and A have the same meanings as above, and reacting the chlorinated or brominated compound with a solvolysis solvent selected from the group consisting of aliphatic alcohols having 1 to 4 carbon atoms, glycols having 2 to 4 carbon atoms, glycerine, acetic acid, propionic acid methylmercaptan, ethylmercaptan and water.

4. A process as claimed in claim 3, wherein the lower alkanoyloxymethyl is acetoxymethyl or propionyloxymethyl.

5. A process as claimed in claim 3, wherein the chlorinating or brominating agent is chlorine, bromine, sulfuryl chloride, sulfuryl bromide, N-chlorosuccinimide, N-bromosuccinimide, N-chlorophthalimide, N-bromophthalimide, t-butyl hypochlorite, trichloroisocyanuric acid, thionyl chloride or thionyl bromide.

6. A process as claimed in claim 3, wherein A is the penicillin moiety as defined in claim 3.

7. A process as claimed in claim 3, wherein A is the cephalosporin moiety as defined in claim 3.

8. A process as claimed in claim 1, wherein the solvolysis solvent is a straight chain monohydric alcohol having 1 to 3 carbon atoms.

9. A process as claimed in claim 8, wherein the straight chain monohydric alcohol is methanol.

10. A process as claimed in claim 1, wherein R¹ is a member selected from the group consisting of phenyl, thienylmethyl, phenoxymethyl, benzyl and 4-amino-4-carboxybutyl whose amino and/or carboxy group is unprotected or protected by a conventional protecting group.

11. A process as claimed in claim 10, wherein the protective group for the amino group of the 4-amino-4-carboxybutyl group is a member selected from the group consisting of phthaloyl, isobornyloxycarbonyl, p-(t-butyl)benzoyl and p-(t-butyl)benzenesulfonyl.

12. A process as claimed in claim 11, wherein the protective group for the carboxy group of the 4-amino-4-carboxybutyl group is a member selected from the group consisting of β-methylsulfonyl ethyl, dimethylsilyl, trimethylsilyl and phosphorous trichloride.

13. A process as claimed in claim 1, wherein A is the cephalosporin moiety.

14. A process as claimed in claim 13, wherein R² is a group represented by the formula

wherein R³ is a 5 or 6 membered nitrogen-containing heterocyclic group having 1 to 4 hetero atoms selected from the group consisting of nitrogen, oxygen and sulfur, which is unsubstituted or substituted by alkyl having 1 to 4 carbon atoms, the nitrogen being in the oxide or non-oxide form.

15. A process as claimed in claim 14, wherein the nitrogen-containing heterocyclic group is a member selected from the group consisting of pyridyl, N-oxido-pyridyl, pyrimidyl, pyridazinyl, N-oxido-pyridazinyl, pyrazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl and 2H-tetrazolyl.

16. A process as claimed in claim 14, wherein R² is a member selected from the group consisting of (1-methyltetrazol-5-yl)thiomethyl, (5-methyl-1,3,4-thiadiazol-2-yl)thiomethyl, (1,3,4-thiadiazol-2-yl)thiomethyl and (5-methyl-1,3,4-oxadiazol-2-yl)thiomethyl.

17. A process as claimed in claim 13, wherein in the starting compound R¹ is 4-t-butylbenzoylamido-4-carboxybutyl, X is chlorine, R² is (1-methyltetrazol-5-yl)thiomethyl and each carboxy group is protected with a dimethylsilyl group.

18. A process as claimed in claim 13, wherein in the starting compound R¹ is 4-phthalimido-4-carboxybutyl, X is chlorine, R² is (1-methyltetrazol-5-yl)thiomethyl and each carboxy group is protected with a dimethylsilyl group.

19. A process as claimed in claim 13, wherein in the starting compound R¹ is 4-t-butylbenzenesulfonamido-4-carboxybutyl, X is chlorine, R² is (1-methyltetrazol-5-yl)thiomethyl and each carboxy group is protected with a dimethylsilyl group.

20. A process as claimed in claim 13, wherein in the starting compound R¹ is 4-isobornyloxycarbonylamido-4-carboxybutyl, X is chlorine, R² is (1-methyltetrazol-5-yl)thiomethyl and each carboxy group is protected with a dimethylsilyl group.

21. A process as claimed in claim 13, wherein in the starting compound R¹ is 4-phthalimido-4-carboxybutyl, X is chlorine, R² is (5-methyl-1,3,4-thiadiazol-2-yl)thiomethyl and each carboxy group is protected with a dimethylsilyl group.

22. A process as claimed in claim 13, wherein in the starting compound R¹ is 4-phthalimido-4-carboxybutyl, X is chlorine, R² is (1,3,4-thiadiazol-2-yl)thiomethyl and each carboxy group is protected with a dimethylsilyl group.

23. A process as claimed in claim 13, wherein in the starting compound R¹ is 4-phthalimido-4-carboxybutyl, X is chlorine, R² is (5-methyl-1,3,4-oxadiazol-2-yl)thiomethyl and each carboxy group is protected with a dimethylsilyl group.

24. A process as claimed in claim 13, wherein in the starting compound R¹ is 4-phthalimido-4-carboxybutyl, X is bromine, R² is (1-methyltetrazol-5-yl)thiomethyl and each carboxy group is protected with a dimethylsilyl group.

25. A process as claimed in claim 13, wherein in the starting compound R¹ is 4-phthalimido-4-carboxybutyl, X is chlorine, R² is (5-carboxymethyl-1,3,4-thiadiazol-2-yl)thiomethyl and each carboxy group is protected with a dimethylsilyl group.

26. A process as claimed in claim 13, wherein in the starting compound R¹ is 4-phthalimido-4-carboxybutyl, X is chlorine, R² is [5-($\beta$-hydroxyethylthio)-1,3,4-thiadiazol-2-yl]thiomethyl and each carboxy group is protected with a dimethylsilyl group.

27. A process as claimed in claim 13, wherein in the starting compound R¹ is 4-phthalimido-4-carboxybutyl, X is chlorine, R² is [5-(N,N-dimethylcarbamoylmethyl)-1,3,4-thiadiazol-2-yl]thiomethyl and each carboxy group is protected with a dimethylsilyl group.

28. A process as claimed in claim 13, wherein in the starting compound R¹ is benzyl, R² is methyl, X is chlorine and the carboxy group is protected with a $\beta$-methylsulfonylethyl group.

29. A process as claimed in claim 13, wherein in the starting compound R¹ is 4-phthalimido-4-carboxybutyl, X is chlorine, R² is acetoxymethyl and each carboxy group is protected with a dimethylsilyl group.

30. A process according to claim 3, wherein 7-amino-3-(1-methyltetrazol-5-yl)thiomethyl-3-cephem-4-carboxylic acid is produced by reacting 7-(D-5-phthalimido-5-carboxyvalerthioamido)-3-(1-methyltetrazol-5-yl)thiomethyl-3-cephem-4-carboxylic acid, whose carboxy groups are protected with dimethylsilyl, with N-chlorosuccinimide, and reacting the resultant compound with methanol.

31. A process according to claim 3 wherein 7-amino-3-(5-methyl-1,3,4-thiadiazol-2-yl)thiomethyl-3-cephem-b 4-carboxylic acid is produced by reacting 7-(D-5-phthalimido-5-carboxyvalerthioamido)-3-(5-methyl-1,3,4-thiadiazol-2-yl) thiomethyl-3-cephem-4-carboxylic acid, whose carboxy groups are protected with dimethylsilyl, with N-chlorosuccinimide, and reacting the resultant compound with methanol.

32. A process according to claim 3, wherein 7-amino-3-(5-methyl-1,3,4-oxadiazol-2-yl)thiomethyl-3-cephem-4-carboxylic acid is produced by reacting 7-(D-5-phthalimido-5-carboxyvalerthioamido)-3-(5-methyl-1,3,4-oxadiazol-2-yl) thiomethyl-3-cephem-4-carboxylic acid, whose carboxy groups are protected with dimethylsilyl, with N-chlorosuccinimide, and reacting the resultant compound with methanol.

33. A process according to claim 3, wherein 7-amino-3-(1,3,4-thiadiazol-2-yl)thiomethyl-3-cephem-4-carboxylic acid is produced by reacting 7-(D-5-phthalimido-5-carboxyvalerthioamido)-3-(1,3,4-thiadiazol-2-yl)thiomethyl-3-cephem-4-carboxylic acid, whose carboxy groups are protected with dimethylsilyl, with N-chlorosuccinimide, and reacting the resultant compound with methanol.

34. A process according to claim 3, wherein 7-amino-3-(1-methyltetrazol-5-yl)thiomethyl-3-cephem-4-carboxylic acid is produced by reacting 7-(D-5-isobornyloxycarbonylamido-5-carboxyvalerthioamido)-3-(1-methyltetrazol-5-yl)thiomethyl-3-cephem-4-carboxylic acid, whose carboxy groups are protected by dimethylsilyl, with N-chlorosuccinimide, and reacting the resultant compound with methanol.

35. A process according to claim 3, wherein 7-amino-3-(1-methyltetrazol-5-yl)thiomethyl-3-cephem-4-carboxylic acid is produced by reacting 7-(D-5-t-butylbenzoylamido-5-carboxyvalerthioamido)-3-(1-methyltetrazol-5-yl)thiomethyl-3-cephem-4-carboxylic acid, whose carboxy groups are protected with dimethylsilyl, with N-chlorosuccinimide, and reacting the resultant compound with methanol.

36. A process according to claim 3, wherein 7-amino-3-(1-methyltetrazol-5-yl)thiomethyl-3-cephem-4-carboxylic acid is produced by reacting 7-(D-5-p-t-butyl-benzenesulfonamido-5-carboxyvalerthioamido)-3-(1-methyltetrazol-5-yl)thiomethyl-3-cephem-4-carboxylic acid, whose carboxy groups are protected by dimethylsilyl, with N-chlorosuccinimide, and reacting the resultant compound with methanol.

37. A process according to claim 1, wherein the alkoxycarbonyl having 2 to 13 carbon atoms is a member selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl; the alkoxy having 1 to 12 carbon atoms is a member selected from the group consisting of methoxy, ethoxy, propoxy, butoxy, isobutoxy, hexyloxy, octyloxy, decyloxy and dodecyloxy; the alkylthio having 1 to 3 carbon atoms is a member selected from the group consisting of methylthio, ethylthio and isopropylthio; the alkylsulfonyl having 1 to 3 carbon atoms is a member selected from the group consisting of methylsulfonyl, ethylsulfonyl and isopropylsulfonyl; and the glycols having 2 to 4 carbon atoms represent a group consisting of ethylene glycol, propylene glycol and 1,3-butanediol.

38. A process according to claim 1, wherein the N-lower alkylamino is N,N-dimethylamino.

39. A process according to claim 3, wherein the alkoxycarbonyl having 2 to 13 carbon atoms is a member selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl; the alkoxy having 1 to 12 carbon atoms is a member selected from the group consisting of methoxy, ethoxy, propoxy, butoxy, isobutoxy, hexyloxy, octyloxy, decyloxy and dodecyloxy; the alkythio having 1 to 3 carbon atoms is a member selected from the group consisting of methylthio, ethylthio and isopropylthio; the alkylsulfonyl having 1 to 3 carbon atoms is a member selected from the group consisting of methylsulfonyl, ethylsulfonyl and isopropylsulfonyl; and the glycols having 2 to 4 carbon atoms represent a group consisting of ethylene glycol, propylene glycol and 1,3-butanediol.

40. A process according to claim 3, wherein the N-lower alkylamino is N,N-dimethylamino.

41. A process according to claim 3, wherein β-methylsulfonylethyl 7-amino-3-desacetoxycephalosporanate is produced by reacting an adduct consisting of β-methylsulfonylethyl 7-phenylthioacetamido-3-desacetoxycephalosporanate, pyridine and hydrogen chloride with bromine, and reacting the resultant compound with methanol.

42. A process according to claim 3, wherein 7-aminocephalosporanic acid is produced by reacting 7-(D-5-phthaloylimido-5-carboxy valerthioamido)-3-acetoxymethyl-3-cephem-4-carboxylic acid, whose carboxy groups are protected by dimethylsilyl, with N-chlorosuccinimide, and reacting the resultant compound with methanol.

* * * * *

UNITED STATES PATENT OFFICE
CERTIFICATE OF CORRECTION

Patent No. 4,068,072          Dated January 10, 1978

Inventor(s) Susumu Tsushima; Norichika Matsumoto and Mitsuo Numata

It is certified that error appears in the above-identified patent and that said Letters Patent are hereby corrected as shown below:

In the heading of the Patent under the section entitled "[30] Foreign Application Priority Data", change "48-1171" to --49-1171--.

*Signed and Sealed this*

*Twenty-third* Day of *May 1978*

[SEAL]

Attest:

RUTH C. MASON
*Attesting Officer*

LUTRELLE F. PARKER
*Acting Commissioner of Patents and Trademarks*